United States Patent [19]
Gildersleeve et al.

[11] Patent Number: 6,117,164
[45] Date of Patent: Sep. 12, 2000

[54] FLEXIBLE MULTIJOINT THERAPEUTIC PADS

[75] Inventors: Richard Earle Gildersleeve, Escondido; David Winer, Vista, both of Calif.

[73] Assignee: DJ Orthopedics, LLC, Vista, Calif.

[21] Appl. No.: 08/870,868

[22] Filed: Jun. 6, 1997

[51] Int. Cl.$^7$ ....................................................... A61F 7/00
[52] U.S. Cl. ........................... 607/108; 607/112; 607/114
[58] Field of Search ............................. 607/104, 108–112, 607/114; 165/46; 126/204

[56] References Cited

U.S. PATENT DOCUMENTS

| | | |
|---|---|---|
| 267,435 | 11/1882 | Leiter . |
| D. 340,526 | 10/1993 | Molloy . |
| D. 345,609 | 3/1994 | Mason et al. . |
| D. 345,802 | 4/1994 | Mason et al. . |
| D. 345,803 | 4/1994 | Mason et al. . |

(List continued on next page.)

FOREIGN PATENT DOCUMENTS

| | | |
|---|---|---|
| 0 535 830 A1 | 4/1993 | European Pat. Off. . |
| 0 560 309 A1 | 9/1993 | European Pat. Off. . |
| 142148 | 6/1980 | Germany . |
| 1090339A | 5/1985 | Russian Federation . |
| 1404058A1 | 6/1988 | Russian Federation . |
| WO 88/04536 | 6/1988 | WIPO . |
| WO 94/00086 | 1/1994 | WIPO . |

OTHER PUBLICATIONS

McAdams, et al., Transmission of Heat by Conduction and Convection, pp. 4–90–4–107, (undated).
McAdams, "Heat Transmission," Sponsored by the Committee on Heat Transmission National Research Council, McGraw–Hill Book Company, Inc., Third Edition (1954).
Lyons and Askland, *Lyons Encyclopedia of Values*, pp. 48–49 (1975).
Breg Packaging"Contents 1: Cold Therapy Pad", PN 1.00473 REV A Apr. 1996.
Polar Pump Retaining Bracket, Jan. 1992.
Albin, et al., Localized Spinal Cord Hypothermia, (undated).
"Healthcore Introduces the Dr. Kirt Josefek OMNIPAK ™ The Cold/Hot Support Compress That Brings Total Versatility to Cold or Hot Treatments on any Part of the Body" (undated).

(List continued on next page.)

*Primary Examiner*—Cary O'Connor
*Assistant Examiner*—Ryan Carter
*Attorney, Agent, or Firm*—Knobbe, Martens, Olson & Bear, LLP.

[57] ABSTRACT

Flexible multijoint thermal therapy pads which are dimensioned and structured to promote effective thermal therapy by promoting increased flexibility, comfort, convenience and heat transfer when applied to a range of joints in the body. Pads according to the present invention feature distinct members each of which corresponds to and may be applied to conform to a limb or body part surrounding the knee, shoulder and other joints. The pads connect these members using at least one conduit that is not substantially centered on the kneecap or top of the shoulder when they are applied for thermal therapy on the knee or shoulder, respectively. The pads thus do not blindly adhere to traditional multijoint notions of symmetry, but instead opt for increased flexibility, prevention of undesired blockage or occlusion during joint flexure and restriction of range of motion. Pad structures according to the present invention also may be employed to regulate, on a localized basis, thermal medium local velocity at desired points within the pads to deliver a greater or a lesser heat transfer rate at desired areas such as adjacent to the patella in the knee or the humeral head in the shoulder. Increased flexibility, comfort, convenience and optimum heat transfer increase the chances that patients will persist in the full course of thermal therapy in order to promote more effective healing in a shorter period of time.

38 Claims, 5 Drawing Sheets

U.S. PATENT DOCUMENTS

| | | |
|---|---|---|
| D. 352,781 | 11/1994 | Mason et al. . |
| D. 383,848 | 9/1997 | Mason et al. . |
| 500,568 | 7/1893 | Ells . |
| 691,270 | 1/1902 | Jones . |
| 787,920 | 4/1905 | Hofmann . |
| 984,452 | 2/1911 | Teeter . |
| 1,004,192 | 9/1911 | Phelan . |
| 1,011,606 | 12/1911 | Fulton . |
| 1,129,081 | 2/1915 | Edmonds . |
| 1,130,072 | 3/1915 | Donovan et al. . |
| 1,268,002 | 5/1918 | Goodwin . |
| 1,622,903 | 3/1927 | Cox . |
| 1,636,568 | 7/1927 | Kennedy . |
| 1,640,014 | 8/1927 | Tomasulo . |
| 1,940,014 | 12/1933 | Petty . |
| 2,026,747 | 1/1936 | Nemzek . |
| 2,299,162 | 10/1942 | Marick . |
| 2,726,658 | 12/1955 | Chessey . |
| 2,930,594 | 3/1960 | MacCracken . |
| 3,017,888 | 1/1962 | Weiner . |
| 3,061,242 | 10/1962 | Zurawinski et al. . |
| 3,091,242 | 5/1963 | Johnson, Jr. et al. . |
| 3,247,851 | 4/1966 | Seibert . |
| 3,297,034 | 1/1967 | Peavy . |
| 3,425,419 | 2/1969 | Dato . |
| 3,548,819 | 12/1970 | Davis et al. . |
| 3,683,902 | 8/1972 | Artemenko et al. . |
| 3,738,367 | 6/1973 | Hardy . |
| 3,744,555 | 7/1973 | Fletcher et al. . |
| 3,791,767 | 2/1974 | Shill . |
| 3,832,780 | 9/1974 | Lewis . |
| 3,866,608 | 2/1975 | Reynolds et al. . |
| 3,867,939 | 2/1975 | Moore et al. . |
| 3,871,381 | 3/1975 | Roslonski . |
| 3,889,684 | 6/1975 | Lebold . |
| 3,896,794 | 7/1975 | McGrath . |
| 3,901,225 | 8/1975 | Sconce . |
| 3,916,911 | 11/1975 | Sauder et al. . |
| 3,918,458 | 11/1975 | Nethery . |
| 3,942,518 | 3/1976 | Tenteris et al. . |
| 3,967,627 | 7/1976 | Brown . |
| 3,993,053 | 11/1976 | Grossan . |
| 3,995,621 | 12/1976 | Fletcher et al. . |
| 4,010,795 | 3/1977 | Stenberg . |
| 4,026,229 | 5/1977 | Winbeg . |
| 4,026,299 | 5/1977 | Sauder . |
| 4,061,898 | 12/1977 | Murray et al. . |
| 4,108,146 | 8/1978 | Golden . |
| 4,112,943 | 9/1978 | Adams . |
| 4,114,620 | 9/1978 | Moore et al. . |
| 4,149,529 | 4/1979 | Copeland et al. . |
| 4,149,541 | 4/1979 | Gammons et al. . |
| 4,170,998 | 10/1979 | Sauder . |
| 4,184,537 | 1/1980 | Sauder . |
| 4,190,054 | 2/1980 | Brennan . |
| 4,201,226 | 5/1980 | Phillips . |
| 4,202,325 | 5/1980 | Villari et al. . |
| 4,233,967 | 11/1980 | Daniell, Jr. . |
| 4,271,831 | 6/1981 | Deibert . |
| 4,312,335 | 1/1982 | Daniell, Jr. . |
| 4,335,726 | 6/1982 | Kolstedt . |
| 4,338,944 | 7/1982 | Arkans . |
| 4,357,009 | 11/1982 | Baker . |
| 4,382,446 | 5/1983 | Truelock et al. . |
| 4,397,315 | 8/1983 | Truelock et al. . |
| 4,459,468 | 7/1984 | Bailey . |
| 4,481,941 | 11/1984 | Rolfes . |
| 4,493,316 | 1/1985 | Reed et al. . |
| 4,523,594 | 6/1985 | Kuznetz . |
| 4,531,515 | 7/1985 | Rolfes . |
| 4,532,594 | 7/1985 | Hosaka et al. . |
| 4,575,097 | 3/1986 | Brannigan et al. . |
| 4,587,959 | 5/1986 | Ruderian . |
| 4,643,176 | 2/1987 | Mason et al. . |
| 4,649,934 | 3/1987 | Fraser et al. . |
| 4,681,097 | 7/1987 | Pansiera . |
| 4,691,762 | 9/1987 | Elkins et al. . |
| 4,697,583 | 10/1987 | Mason et al. . |
| 4,706,658 | 11/1987 | Cronin . |
| 4,745,922 | 5/1988 | Taylor . |
| 4,753,241 | 6/1988 | Brannigan et al. . |
| 4,756,310 | 7/1988 | Bitterly . |
| 4,776,558 | 10/1988 | Bellini . |
| 4,800,867 | 1/1989 | Owens . |
| 4,805,620 | 2/1989 | Meistrell . |
| 4,821,354 | 4/1989 | Little . |
| 4,834,057 | 5/1989 | McLeod, Jr. . |
| 4,844,072 | 7/1989 | French et al. . |
| 4,846,176 | 7/1989 | Golden . |
| 4,947,843 | 8/1990 | Wright et al. . |
| 4,962,761 | 10/1990 | Golden . |
| 4,971,056 | 11/1990 | Seacord . |
| 4,979,375 | 12/1990 | Nathans et al. . |
| 4,989,337 | 2/1991 | Mason et al. . |
| 5,014,695 | 5/1991 | Benak et al. . |
| 5,051,562 | 9/1991 | Bailey et al. . |
| 5,072,875 | 12/1991 | Zacoi . |
| 5,074,285 | 12/1991 | Wright . |
| 5,080,089 | 1/1992 | Mason et al. . |
| 5,086,771 | 2/1992 | Molloy . |
| 5,086,772 | 2/1992 | Larnard et al. . |
| 5,088,478 | 2/1992 | Grim . |
| 5,097,829 | 3/1992 | Quisenberry . |
| 5,106,373 | 4/1992 | Augustine et al. . |
| 5,133,348 | 7/1992 | Mayn . |
| 5,148,606 | 9/1992 | Mason et al. . |
| 5,170,783 | 12/1992 | Smith . |
| 5,172,689 | 12/1992 | Wright . |
| 5,174,285 | 12/1992 | Fontenot . |
| 5,190,032 | 3/1993 | Zacoi . |
| 5,230,335 | 7/1993 | Johnson, Jr. et al. . |
| 5,232,020 | 8/1993 | Mason et al. . |
| 5,241,951 | 9/1993 | Mason et al. . |
| 5,241,959 | 9/1993 | Kim et al. . |
| 5,259,379 | 11/1993 | Kim et al. . |
| 5,259,587 | 11/1993 | D'Alessio et al. . |
| 5,277,695 | 1/1994 | Johnson, Jr. et al. . |
| 5,297,773 | 3/1994 | Collins et al. . |
| 5,314,455 | 5/1994 | Johnson, Jr. et al. . |
| 5,324,318 | 6/1994 | Smith . |
| 5,324,319 | 6/1994 | Mason et al. . |
| 5,330,519 | 7/1994 | Mason et al. . |
| 5,336,249 | 8/1994 | Mahawili . |
| 5,344,436 | 9/1994 | Fontenot et al. . |

| | | |
|---|---|---|
| 5,352,214 | 10/1994 | Oscarsson . |
| 5,395,399 | 3/1995 | Rosenwald . |
| 5,402,823 | 4/1995 | Cole . |
| 5,411,432 | 5/1995 | Wyatt et al. . |
| 5,411,541 | 5/1995 | Bell et al. . |
| 5,411,542 | 5/1995 | Jensen . |
| 5,417,720 | 5/1995 | Mason . |
| 5,441,533 | 8/1995 | Johnson et al. . |
| 5,449,379 | 9/1995 | Hadtke . |
| 5,456,701 | 10/1995 | Stout . |
| 5,458,581 | 10/1995 | Hull . |
| 5,466,250 | 11/1995 | Johnson, Jr. et al. . |
| 5,470,353 | 11/1995 | Jensen ................................ 607/114 X |
| 5,476,489 | 12/1995 | Koewler . |
| 5,476,490 | 12/1995 | Silver ...................................... 607/108 |
| 5,486,207 | 1/1996 | Mahawili . |
| 5,496,357 | 3/1996 | Jensen et al. . |
| 5,496,358 | 3/1996 | Rosenwald . |
| 5,507,792 | 4/1996 | Mason et al. . |
| 5,534,021 | 7/1996 | Dvoretzky et al. . |
| 5,662,695 | 9/1997 | Mason et al. . |

OTHER PUBLICATIONS

"Coming Into Increasing Use . . . Stainless Steel as Stirrup Material," *Braces Today*, (Apr. 1951).

Atlas of orthotic Biomechanical Principles and Application, American Academy of Orthopaedic Surgeons (Publisher, The C.V. Mosby Company, Saint Louis), pp. 187–191 (1975).

Orthopaedic Appliances Atlas, vol. 1, Braces Splints Shoe Alterations, A Consideration of Aids Employed in the Practice of Orthopaedic Surgery, (Publisher, J. W. Edwards, Ann Arbor, Michigan), pp. 411–415, 542–543, 1952).

"Section 2.2 Centrifugal Pump Construction," Pump Handbook, Edited by Karassik, Krutzsch, Fraser, Second Edition (Publisher, McGraw–Hill Book Company), pp. 2.33–2.35, 1985).

The American Institute of Architects, Architectual Standards, Seventh Edition, Edited by Robert T. Packard, AIA (Publisher, John Wiley & Sons, Inc.), pp. 632, 634, 635, 1981.

FLEXIBLE MULTIJOINT THERAPEUTIC PADS

FIELD OF THE INVENTION

The present invention relates to multijoint flexible therapeutic pads which act as heat exchangers for delivering thermal gradients to the knee, shoulder and other parts of the body.

BACKGROUND OF THE INVENTION

Effectiveness of thermal therapy in post trauma and post surgical settings continues to engender a variety of thermal therapy systems. (The term "thermal therapy" for purposes of this document means therapy which induces hypothermia or hypothermia, cold or heat, to the body or a part of it, whether extradurally or otherwise.) The precise mechanics of thermal therapy remain the subject of debate and research. The literature indicates that cold therapy can, for instance, reduce swelling, inflammation, edema and ischemic damage due to vascular or arterial compromise. Cold therapy is also said as a general matter to aid in control and management of tissue hypoxia that can otherwise be a manifestation of impaired oxygen diffusion or compromised circulation. It also is generally recognized to reduce pain and reduce the need for pain relief medication.

Recent developments in thermal therapy systems include patient portable systems which employ a small ice chest connected to a flexible heat exchanger or thermal therapy pad via a pair of tubes. A pump, which may be located in the ice chest, supplies chilled fluid to an inlet port of the pad. An exhaust port connected to an exhaust tube carries the fluid, or a portion of it, in a return loop to the ice chest. Temperature within the pad may be regulated in a number of ways. A valve may be employed to control the flow rate in the pad inlet or exhaust, and/or to recirculate a portion of the exhaust fluid.

In physical therapy, as in many things, effectiveness of treatment is largely a function of convenience and comfort. Portable thermal therapy systems accordingly enjoy increased popularity to a major degree because their increased convenience promotes the patient's actually adhering to the therapy program. Such systems, for instance, eliminate the need constantly to replenish an ice pack with a new supply of ice, endure the chore of a weighty and cumbersome ice pack on the knee or shoulder, and the added bother of interposing a towel, with its inevitable sogginess, to mediate between the freezing ice cubes and the skin. Conventional thermal therapy systems instead use a thinner, lighter, flexible pad with a reasonably but not overly cold temperature. The patient may carry the ice chest with its own battery pack in order to supply circulation of the chilled fluid to the pad, or when able to access an electrical outlet, rely on the power grid using a power converter.

Because efficacy of physical therapy and cold therapy in particular is largely a function of convenience, conventional thermal therapy systems present significant additional potential for improvement and design breakthroughs. Because patients tend to abandon the course of thermal therapy treatment if it is inconvenient or uncomfortable, it is critical to ensure that the flexible therapeutic pad of such systems is comfortable to the patient, promotes convenience, and is minimally intrusive to the patient's flexibility and mobility. Patients will be inclined to discontinue the therapy if the pad, for instance, overly restricts mobility of the joint, must be continually reapplied, requires undue attention and readjustment, feels uncomfortable, or is otherwise cumbersome, awkward or inconvenient.

On another more immediate level, effectiveness of the heat transfer imparted by the flexible therapy pad may suffer if a thermal therapy pad becomes occluded as it is placed on the joint or as it flexes with the joint. Some conventional pads are shaped in a manner that causes internal blockage when placed on the joint or as the knee or shoulder flexes; such blockage restricts fluid flow in at least parts of the pads and thus deprives portions of the body surface of effective thermal therapy. Moreover, some conventional pads lose contact with areas of the skin when initially placed on the knee or shoulder or when the knee or shoulder is flexed and the pads fail effectively to conform to the body surface through the appropriate range of flexion. Accordingly, increased flexibility of the therapy pad must not be undertaken at the expense of effective heat transfer.

Previous flexible therapeutic pads employed in cold therapy systems recognize the value of a thinner pad per se but they generally adhere gratuitously to notions of symmetry. For instance, the pad disclosed in U.S. Pat. No. 5,086,771 issued Feb. 11, 1992 to Molloy and U.S. Pat. No. 5,417,720 issued May 23, 1995 to Mason, are symmetrical about their center axis. Although symmetry appeals intrinsically to the intellect, the present invention does not blindly bow to or adopt symmetry in flexible therapeutic pad topology. In that respect, U.S. Pat. Nos. 5,411,542 issued May 2, 1995 and 5,470,353 issued Nov. 28, 1995 to Jensen show asymmetrical thermal therapy pads, but in a way specifically tailored to the ankle and shoulder joint, respectively. Such specialized pads can provide comfort, convenience and more effective heat transfer through a better fit, but requiring separate pads for the ankle and shoulder presents added design, manufacturing, distribution, inventory and tracking expense because, among other things, a number of different pad designs must be supported throughout this entire chain rather than a single pad design which can accommodate various joints.

Conventional flexible therapeutic pads as described in the Mason and Molloy patents feature inlet and exhaust ports on the center line about which the pads are symmetrical. It is a given that the inlet and exhaust tubes to which the ports are connected must be oriented, for purposes of convenience, generally on the limb, such as for instance, either up the limb or down it, in order to avoid cantilevering the tubes into mid-air and subjecting them to physical interference, inconvenience, excessive wear and abuse. The axis of symmetry of the conventional multijoint pads being aligned with the tubes requires these conventional symmetrical pads to extend continuously and uninterrupted along the proximal/distal axis across the patella or shoulder joint. Flexure of the knee or shoulder causes buckling of such a pad along its center line. The buckling of such pads and concomitant failure effectively to conform to the limb as it flexes can not only cause internal occlusion or blockage within parts of the pad to obstruct fluid flow and render at least a part of the pad ineffectual for thermal therapy; it can also naturally separate the heat exchanger from the body to reduce effectiveness of the cold therapy, create discomfort, and introduce resistance to joint flexure and mobility.

Pads of the present invention, by contrast, feature at least two members which are adapted in shape to conform to body parts that surround the knee, shoulder or other joint, but which members are in fluid communication via a conduit whose centerline does not overlie the patella or the top of the shoulder, or which is not substantially centered on the patella as the joint flexes. Centering of the conduit to one side of the patella or top of the shoulder, the inventors have found, makes a substantial difference in providing flexible fit, form and function without compromise of effective fluid flow in all areas of the pad and consequent effectiveness of thermal therapy imparted by the pad. Positioning the conduit that connects these members may be carried out, for example, by introducing, according to the present invention, gaps, clefts or other peripheral discontinuities which could, for example and if desired (but not necessarily), overlie and intersect the limb proximal/distal axis in order to increase flexure of the pad without compromising other value properties.

The present invention also exploits the opportunity to optimize flow velocity at predetermined points within a flexible therapeutic pad, unlike conventional pads, in order to accentuate local heat transfer rate where appropriate. The inventors believe, and their experiences tend to show, that they can adjust and create flow restrictions at desired points within the pads in order to regulate local flow velocity and affect heat transfer rate where the knee or shoulder needs it. For instance, the inventors believe that increasing local flow velocity closer to the interior of the pad as a general matter can promote a greater heat transfer rate at the site of injury or surgery, with reduced heat transfer at the perimeter of the site. Such variable heat transfer rates can be particularly useful in applications where inflammation, edema, ischemia and/or swelling is local in nature.

SUMMARY OF THE INVENTION

The present invention provides flexible therapeutic pads which are adapted to accommodate the knee joint and the shoulder joint, together with other joints if desired. Like previous pads, they may be formed with a first layer of flexible material of a desired shape whose periphery is bonded, heat welded or otherwise joined to the periphery of a second layer of flexible material in order to form a heat exchanger which may be applied to the patient's body. Other layers may be added, such as a foam layer, and a hook or loop layer for securing the pad to the body. An inlet port and an exhaust port feed a fluid or other thermal medium to the pad and remove it, respectively, in order to create the thermal differential which is applied to the pad/tissue interface in order to induce heat transfer. (The term "heat transfer" means flow of thermal energy from hot to cold and, as part of that process, flow of lower thermal energy state from cold to hot. The term as used in this document contemplates any transfer or flow of thermal energy, or lack of it, to induce hypothermia or hypothermia extradurally or otherwise.)

Unlike previous multijoint flexible therapeutic pads, however, pads according to the present invention need not be symmetrical along their center line but instead can focus on providing at least two members each of which is adapted to conform to a part of the leg adjacent to the knee, or the arm or torso in the case of the shoulder. The members are in fluid communication with each other through at least one conduit whose center does not overlie the patella or the top of the shoulder, or which is not substantially centered on the patella or top of the shoulder as the joint flexes. Centering of the conduit to one side of the patella or top of the shoulder makes a substantial difference in providing flexible fit, form and function without compromise of effective fluid flow in all areas of the pad and consequent effectiveness of thermal therapy imparted by the pad. A pad with such members and conduit may be formed, for instance (but not necessarily) by introducing peripheral deep discontinuities, such as to overlie the proximal/distal axis of the patient's limb in order to promote flexibility whether or not notions of symmetry are abandoned. According to one aspect of the invention, flexible therapeutic pads as viewed in plan accommodate multiple joints in a patient by including a first member, a second member in fluid communication with the first member through a conduit that is not substantially centered on the patella when the pad is applied for thermal therapy to the knee or the top of the shoulder when the pad is applied for thermal therapy to the shoulder, and an inlet and exhaust port communicating with one of the members so that the inlet and exhaust ports may be oriented generally on the limb (and thus not unduly cantilevered into midair) in a manner that allows: one of the first and second members to conform itself, at least partially, about a portion of the limb or body part on a first side of the joint onto which the other member is not conformed; (2) the other member to conform itself to the limb or body part on the other side of the joint; and, accordingly, (3) adherence of the pad to the joint in a manner that promotes effective contact while the joint is static and that permits the joint to flex without substantially disturbing the conformity of the pad members to the limb and body parts, while minimizing occlusion in the pad or areas of it, and thus without substantially comprising the comfort of the pad, the effectiveness of the heat transfer induced by the pad, and the flexibility and mobility of the patient's joint.

The pads according to the present invention also may contain flow restrictions in order to regulate local thermal medium or fluid velocity at predetermined locations in order to regulate heat transfer rates locally within the pad. One or more flow path boundaries, formed by heat welding, bonding, or otherwise, create fluid flow paths within the pads. Such boundaries may be formed in a manner to reduce the flow path cross-sectional area in order to increase local fluid velocity and thus local heat transfer rate. Such flow path restrictions may occur according to the general dimensions of flow path channels created by such boundaries or additional flow path regulators such as spot welds or other structure. As a result, accentuated heat transfer rates may be induced at desired points within the joint such as directly medial and superior to the patella in an acute knee injury.

It is accordingly an object of the present invention to provide flexible therapeutic pads which are shaped to adhere to the knee joint and shoulder joint and surrounding limbs while static or throughout a broad range of motion, with minimum compromise of the flexibility, convenience and comfort.

It is an additional object of the present invention to provide flexible therapeutic pads which are shaped to adhere to the knee joint and shoulder joint and surrounding limbs while static or throughout a broad range of motion, with minimum tendency to form internal occlusion or blockage which would preclude or reduce fluid flow in a manner that substantially adversely affects fluid flow and effectiveness of thermal therapy imparted by the pad.

It is another object of the present invention to provide multijoint flexible therapeutic pads which eschew gratuitous notions of symmetry in favor of the need to introduce peripheral discontinuities along the proximal/distal axis of the patient's limb in order to promote pad flexibility, joint flexibility and mobility, convenience, comfort and effective heat transfer induced by the pad.

It is another object of the present invention to provide multijoint flexible therapeutic pads which feature a number of members each of which may be attached and conformed to a separate limb portion or body part in the vicinity of the joint in order to promote flexibility, convenience, comfort and effective heat transfer.

It is another object of the present invention to provide a flexible therapeutic pad which is shaped and structured to accommodate the knee joint, the shoulder joint and other joints, and which departs from notions of symmetry previously manifested in conventional multijoint flexible therapeutic pads in favor of an asymmetrical shape that promotes flexibility of the pad and joint, increased comfort and convenience and more effective heat transfer.

It is an additional object of the present invention to provide a flexible therapeutic pad which is adapted in shape to accommodate a range of joints in the body with superior fit, form and function, and which can be manufactured inexpensively in order to be competitive in the changing marketplace.

It is an additional object of the present invention to provide multijoint flexible therapeutic pads which feature flow regulation structure at pre-determined points within the pads in order to regulate local fluid velocity, and, accordingly, local heat transfer rates at predetermined points within the joint or body part.

It is an additional object of the present invention to provide thermal therapy pads which are more likely to be employed by the patient over the full range of prescribed therapy because they are more flexible, comfortable and convenient than previously existing flexible therapeutic pads.

Other objects, features and advantages of the present invention will become apparent with respect to the remainder of this document.

DETAILED DESCRIPTION OF THE INVENTION

Figure 1A:
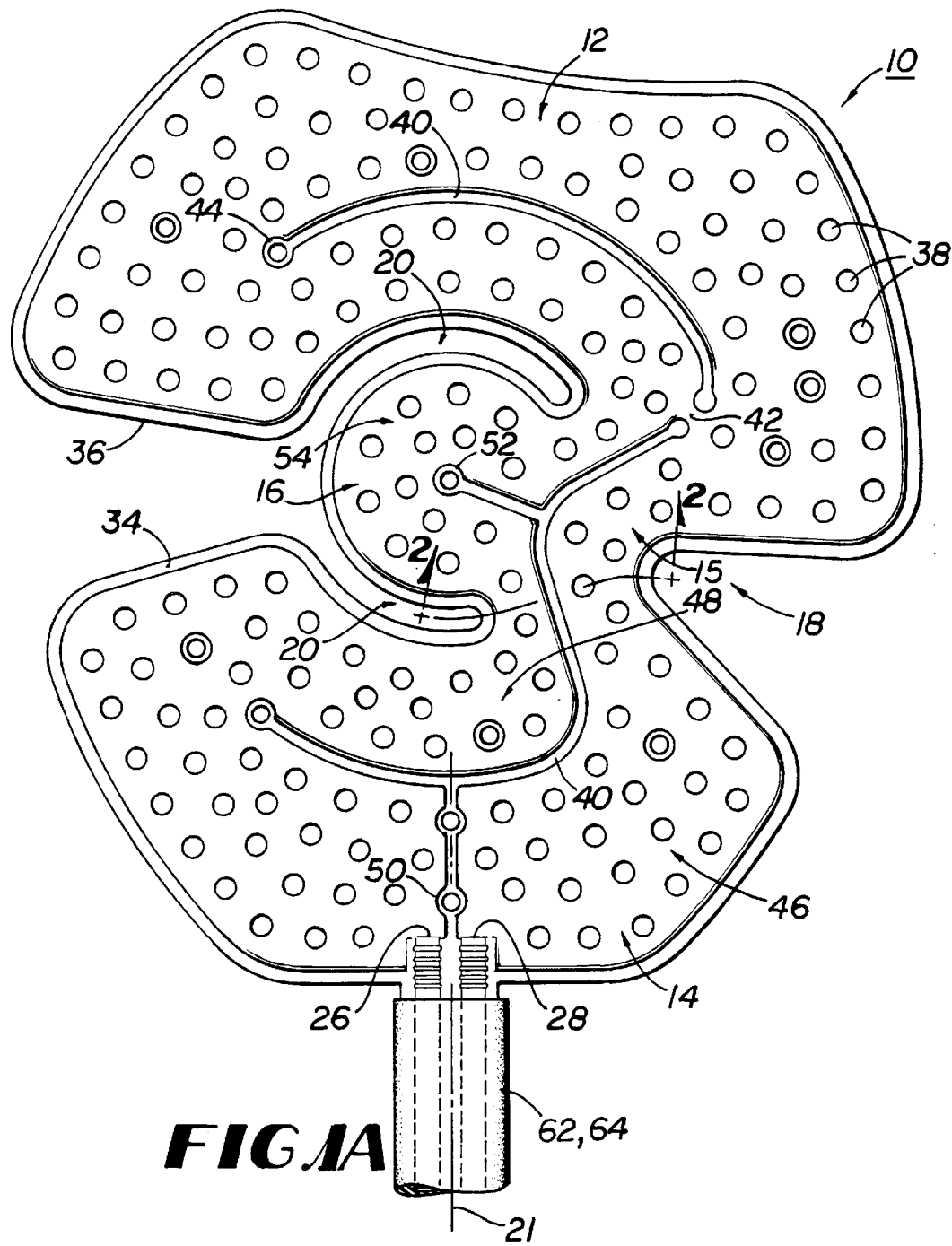
FIG. 1A shows a plan view of a preferred embodiment of a flexible therapeutic pad according to the present invention.

FIG. 1 shows a plan view of a preferred embodiment of flexible therapeutic pads according to the present invention. Pad 10 as shown in FIG. 1 in plan aspect may be considered to resemble the Greek capital letter Sigma, the English letter E, the numeral 3, or other similar shape, whether or not alphanumeric in nature. (Such letters, numbers or shapes are presumed in this document to be interchangeable and simply heuristic, and nothing stated or implied in this document should be construed to restrict shape, structure, configuration or function of pads necessarily to conform, correspond or otherwise be limited to an alphanumeric character, shape or portion thereof, or what it can or cannot do or what something shaped like it can or cannot do.)

A first member 12 corresponds to the upper stroke of the Sigma and, if desired, also the serif. First member 12 may be substantially straight, curved, or any other desired shape which promotes its ability to wrap about or otherwise conform to all or part of a patient's leg, shoulder or other body member on a first side of the knee or shoulder (above or below it). Unlike previous multiple joint flexible therapeutic pads, the emphasis is not on symmetry but rather optimization of the shape and flexibility of first member 12 to conform to its corresponding limb or body member. A second member 14 shown in FIGS. 1A to 1C is similarly shaped and can correspond to the lower stroke (and, if desired, serif) of the Sigma and is configured to conform to a corresponding body part as is first member 12.

A conduit 15 connects members 12 and 14, as shown in the Figures. Conduit 15 provides fluid communication between members 12 and 14, but not in a manner that would cause conduit 15 to pinch or otherwise become occluded while the joint is static or as the joint flexes, as tends to happen in some conventional multijoint pad designs which are symmetrical in shape. Instead, unlike those designs, the conduit 15 and its connection of members 12 and 14 is not substantially centered on (its center does not overlie) the patella or the top of the shoulder so that the pad 10, conduit 15 and members 12 and 14 are less likely to become occluded during use of the pad as the joint flexes. Such off center topology also creates the potential of adding flexibility and further enhancing form, fit, function and effectiveness in imparting thermal therapy, with no or minimal additional risk of occlusion, by introducing clefts and other discontinuities in the perimeter of the pads 10 as disclosed below.

Pads 10 according to the present invention, may, but need not, contain a third, center member 16. Center member 16 can be employed to overlay, conform, or otherwise correspond to a central part of a joint such as the patella in the knee joint and the humeral head in the shoulder. Center member 16 as shown in FIGS. 1A to 1C can correspond in location to the stem point of the Sigma. FIGS. 1A to 1C also shows pad 10 featuring a cleft or indentation 18 which may be generally aligned with center member 16 or as otherwise desired in order to promote flexibility of the pad and flexibility of the joint along all three axis: proximal/distal, medial/lateral, and anterior/posterior. Cleft 18 may be obviously omitted, or other clefts 18 may also be added in order to promote flexibility of the pad, flexibility of the joint, optimum fluid flow in the pad and other shape and heat transfer properties promotive of maximum flexibility, comfort, convenience and effective heat transfer.

Figure 1B:
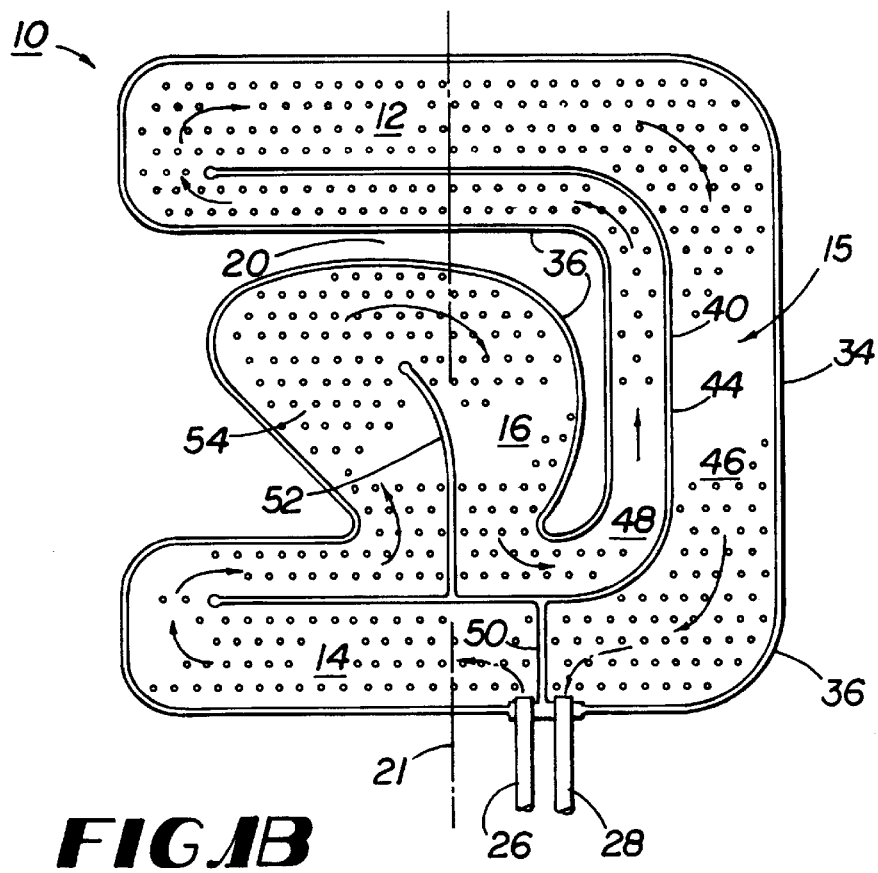
FIG. 1B shows, more schematically, a plan view of a second embodiment of a flexible therapeutic pad according to the present invention.
Figure 1C:
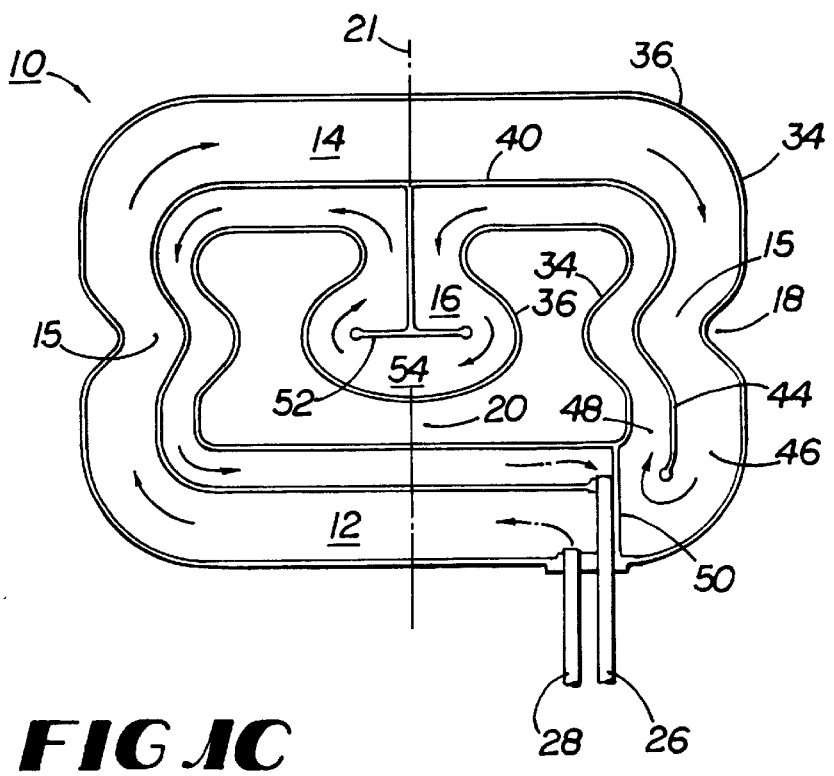
FIG. 1C shows, more schematically, a plan view of a third embodiment of a flexible therapeutic pad according to the present invention.

FIG. 1A shows pad 10 according to the present invention configured generally corresponding to the letter Sigma, but FIGS. 1B and 1C show that pad 10 can be shaped according to the other paradigms. As shown in FIG. 1B, first and second members 12 and 14 can correspond to upper and lower strokes of the letter C and contain a center member 16 which extends from one of the members 12, 14. FIG. 1C shows a design which happens to be generally symmetrical, and which contains two members 12 and 14 which carry out the objectives of the present invention. FIG. 1C also shows there is no reason why members 12 and 14 cannot be connected and in fluid communication, if desired, at both ends, in order to carry out objectives of the present invention.

Pads 10 differ from conventional multijoint pads, such as disclosed in the above-referenced patents, at least to the extent that it has two members which conform to separate body parts on opposite sides of the knee, shoulder or other joint, for thermal therapy to those body parts, and the members are connected by a conduit 15 which is not substantially centered on the patella or the top of the shoulder when the pad is applied to the knee or shoulder for thermal therapy. Accordingly, the user of the pad can be assured that fluid communication (and thus effective heat transfer) within members 12 and 14 will not be inhibited by stretching of the pad over the places on the joint where maximum flexure occurs, such as the patella or top of the shoulder.

Pads according to the present invention can contain peripheral discontinuities in order to create or add to the appropriate asymmetry and topology. That is, when pads 10 according to the present invention are applied to a patient's body, they can be interrupted by space between members 12 and 14 along the proximal/distal axis 19 of the wearer's limb or body part. (Such proximal/distal axis 19, for purposes of this document, may be considered a line on the anterior surface of the user's limb which extends in a substantially proximal and distal direction from substantially the center of the patella, in the knee, and from substantially the center of the acromion in the shoulder.) Put another way, the periphery 36 of the pad can cross the proximal/distal axis 19 of the wearer's limb in more than two places, as can be seen in FIGS. 1A–1C, 4, 4A, 4B, and 5. (Periphery 36 does not simply mean the "outside" edges of the pad; periphery 36, which may form peripheral discontinuities 20, includes any edges at which layers 30, 32 are connected, including "outside" edges and "inside" or "interior" edges as shown in FIG. 1C.) Peripheral discontinuities 20 as shown generally in FIGS. 1A–1C, 4, 4A, 4B, and 5 can occur along that axis 19 as the periphery 36 intersects the proximal/distal axis 19.

The peripheral discontinuities 20 in pads 10 according to the present invention can be considered to correspond to a reason why the conduit 15 lies generally to one side of the patella or top of the shoulder instead of traversing them as the pad is applied to the knee or shoulder, respectively, for thermal therapy. The discontinuities allow members 12 and 14 to adhere to their respective limbs or body members without substantial deformation of pad structure located along the user's limb proximal/distal axis 19 as occurs in previous pads. Similarly, the conduit 15 connecting members 12 and 14 avoids the top of the patella or shoulder and thus does not inhibit flexure of the pad or joint. As one example, the edge or periphery of a conventional pad according to either of the two above-referenced patents only crosses the proximal/distal axis of the limb or, more generally, central locations of the knee or shoulder, at two places so that structure of that pad extends continuously across the anterior surface of the thigh, patella and lower leg, for example, without interruption or discontinuity. If that conventional pad is applied and secured with the knee flexed, then the pad tends to buckle when the knee is straightened. Such buckling separates part of the pad from the knee, since the effective length of the pad along the user's limb proximal/distal axis is now longer than the corresponding segment of that axis itself. If the pad is applied when the knee is straight, then lack of interruption or discontinuity in pad structure allows no room for the pad to expand along the user's limb proximal/distal axis. In either case, the result is bad; ill effects can include occlusion of the pad or parts or areas of it, impairment of heat transfer, discomfort, inconvenience, compromise of joint flexibility and range of motion, and added incentive for the user to abandon the course of thermal therapy.

Pads 10 according to the present invention, by contrast, provide at least two members 12, 14 each of which is adapted to conform to a separate body part surrounding the knee, shoulder or other joint. Conduit 15 which connects them traverses between the body parts to the side of the patella or top of the shoulder, rather than over it. Conduit 15 thus avoids areas of the knee, shoulder or other joint which are subject to maximum deformation as the joint flexes. Accordingly, conduit 15 itself is subject to less deformation during joint flexure and is thus less likely to become occluded or to restrict joint flexure.

Placement of the conduit 15 in this way can be seen to occur in one way, as an example, by introducing gaps, clefts or other discontinuities between members 12 and 14 in the periphery of the pads. These peripheral discontinuities, or at least one of them, could, if desired, overlie the user's limb proximal/distal axis to provide flexion, expansion and contraction of the pad along that axis as the knee or shoulder flexes. FIGS. 4, 4A, 4B and 5 show peripheral discontinuities 20 (which, in those figures, happen to occur between members 12, 14 and center member 16) and how they allow the members 12, 14 to track the motion of the limbs or body parts to which they are attached, the pad surfaces to maintain contact with the skin, and concomitant promotion of flexibility, effective heat transfer, comfort, convenience and overall effective thermal therapy.

As shown in FIG. 1C, inlet 26 and exhaust 28 ports need not be placed on or even near the center line 21 of pad 10. (For purposes of this document, center line 21 of the pad 10 may be considered a line on the pad which overlies the proximal/distal axis 19 of the limb on which the pad is adapted for placement, or it may be a line substantially collinear with a line that runs between inlet 26 and exhaust 28 ports in FIG 1A.) FIG. 1C, for instance, shows inlet 26 and exhaust 28 ports located not on the center line but to the side of the pad 10 so that when it is in use, the ports 26 and 28 and inlet and exhaust tubes 62 and 64 corresponding to them lie along side the limb rather than on the "top" of it (as, for example, on either the medial or lateral aspect of the leg rather than its anterior surface).

Pads 10 according to the present invention may be formed of material conventional to flexible therapy pads and similarly fabricated. As shown in FIGS. 1A–C and FIG. 2, a first layer of flexible material is joined to a second layer of flexible material by RF welding, heat welding or as otherwise desired in order to form pad 10. First layer 30 and second layer 32 are preferably formed of water impermeable material, although not necessarily gas impermeable. A peripheral bond 34 joins the periphery 36 of the layers 30 and 32, which may be RF welded, heat welded or otherwise bonded as desired.

A number of spot bonds or welds 38 may be employed between the two layers 30 and 32, in order to maintain proper thickness and dimensionality to pad 10, and to regulate cross sectional area of pad 10 generally for purposes of controlling fluid flow. They can also function, where desired, to alter the direction or nature of fluid flow in the pad 10. Such structures 38 may be of any desired shape, including, if preferred, of shape and orientation appropriate to impart desired laminar/turbulent characteristics, flow direction and flow velocity to the thermal medium or fluid within pad 10 in order to regulate heat transfer on a localized basis. For instance, some of structures 38 may be elongated corresponding to the direction of flow vectors in the fluid in order to induce laminar flow to the fluid in certain sections of the pad 10 or all of it, or they may be elongated and oriented orthogonal or diagonal to such flow vectors or otherwise dimensioned or oriented to induced turbulence at desired points or in all of pad 10. The elongated structures can be used to reduce the resistance to flow or pressure drop within the pad 10, and thus to lower power requirements for pump 66 output.

First layer 30 and second layer 32 may be formed of the same material, or they may be formed of different materials. Forming the layers 30 and 32 of different materials allows optimum control of expense, flexibility, and thermal conductivity properties among other parameters. For instance, pad 10 could be formed of layers 30 and 32 of different materials, each of which features different heat transfer properties and, if desired, different textures, in order to allow the user a choice of which side of the pad 10 to apply to the skin for maximum comfort and desired induction of cold or heat therapy. Layers 30 and 32 need not be of uniform thickness or thermal conductivity along particular axis; rather, they may be fabricated as desired in order to control and regulate localized heat transfer rates. As pad 10 may be configured to contain flow restrictions in order to promote optimum localized heat transfer at desired points within pad 10, layers 30 and 32 can also be non-uniform across their breadth and length in these respects. A foam layer 33 may be added or laminated to either of the layers 30, 32 for additional comfort and modulation of heat transfer properties of pad 10.

Figure 2:
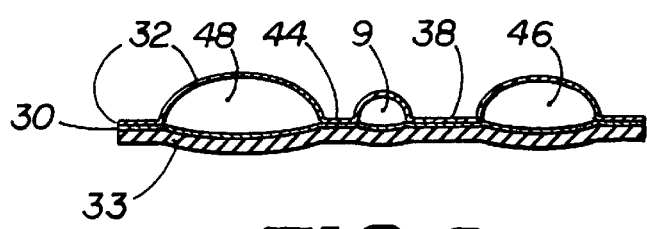
FIG. 2 shows a cross-section of the pad of FIGS. 1A to 1C taken along line 2—2 of FIGS. 1A to 1C.

FIG. 2 shows a cross-sectional view of pad 10 taken along line 2—2. Fluid 9 is shown flowing between layers 30 and 32. Foam layer 33 underlies layer 30. Structure 38 can be visualized in this drawing to introduce the sort of flow restrictions and discontinuities that can create turbulence and eliminate or reduce, if desired, unwanted fluid 9 film and boundary layer effects which can inhibit effective heat transfer.

FIGS. 1A–C also show flow boundaries 40 formed in pads 10. Flow boundaries 40 may be formed by heat welding layers 30 and 32 together or as otherwise desired, and they may be continuous or interrupted with relief or flow diversion gaps 42. In the pad shown in FIG. 1A for instance, a peripheral flow boundary 44 extends into first member 12 and second member 14 in order to define a peripheral flow path 46 and a middle flow path 48. In that pad, fluid entering the pad 10 from inlet port 26 may be diverted from an optional differential boundary 50 to flow through middle flow path 48, around the interior portions of first member 12 and second member 14 in that flowpath, and back toward exhaust port 28 by a peripheral flow path 46.

An interior flow path boundary 52 can form an interior flow path 54, a third flow path in pad 10 and central member 16, if desired. Differential boundary 50 and interior boundary 52 may be joined to peripheral boundary 44, or they may be separated by a gap, boundary, or other separation if desired. All of the boundaries 40 are preferably substantially continuous, but they can contain relief gaps 42 or other discontinuities as desired.

Flow boundaries 40 may be positioned as desired in order effectively to channel or control flow of thermal medium or fluid 9 within the pad 10. FIGS. 1A and B show a single loop circuit formed by a first interior flow path 54, a second middle flow path 48, and the third peripheral flow path 46. The fluid in these pads travels a single outbound and return loop or circuit through the pad, from inlet port 26 to exhaust port 28. FIG. 1C shows a structure in which the circuit traveled by the fluid comprehends substantially a full circle.

FIGS. 1A–C show points at which the cross-section of a flow path are smaller than cross-sections of the flow path at other points. For example, along line 2—2 of FIG. 1, the cross-sectional area of middle flow path 48 appears approximately two-thirds the cross-sectional area of peripheral flow path 46. Smaller cross-sectional area corresponds generally linearly (ignoring boundary layer, film and similar effects) to fluid velocity at such points, the flow rate of fluid 9 remaining constant. Increased fluid velocity can reduce boundary layer and film coefficient effects in addition to increasing heat transfer rate. Although the relationship between fluid velocity and heat transfer rate is a complex one and empirically determined in the face of a number of assumptions (many of which involve effects which can be assumed nonsubstantial), heat transfer rate is at least ideally an exponential function of flow velocity, for fluids such as water, the exponent being generally substantially smaller than one. Accordingly, if fluid velocity increases by, for example, 50%, such as may happen at points in the middle flow path 48 compared to the peripheral flow path 46 on line 2—2 of FIG. 1, the heat transfer rate increases substantially even if by less than that percentage as an empirical matter.

As a general matter, in the pads shown in FIGS. 1A–C, the interior flow path 54 and/or middle flow path 48 are, on the average, smaller in cross-sectional area than the peripheral flow path 46. Accordingly, given that the flow rate in such pads is on the order of approximately 2–8 gallons per hour and given potential fluid temperatures ranging from substantially freezing to room temperature, but preferably in the range of approximately 40 degrees, the heat transfer rates in the internal path 54 and middle flow path 48 can generally and confidently be said to exceed those in peripheral flow path 46. Greater heat transfer rates may therefore be introduced in the areas of, for example, the patella in the knee and humeral head in the shoulder. Accordingly, greater heat transfer rates can be introduced in the areas of the knee or shoulder joint where localized swelling or pain is found. In the knee joint, for instance, the patella, tibial plateau and femoral condyles can receive increased heat transfer assuming they are properly covered by pad 10, because of increased flow velocity in those areas within pad 10. If desired, structures 38 may be introduced in pad 10 to increase fluid flow velocity and thus heat transfer rate in areas corresponding to important ligaments and/or anterior cruciate ligament graft harvest sites such as, for example, the patella tendon in the knee extensor mechanism.

Figure 3:
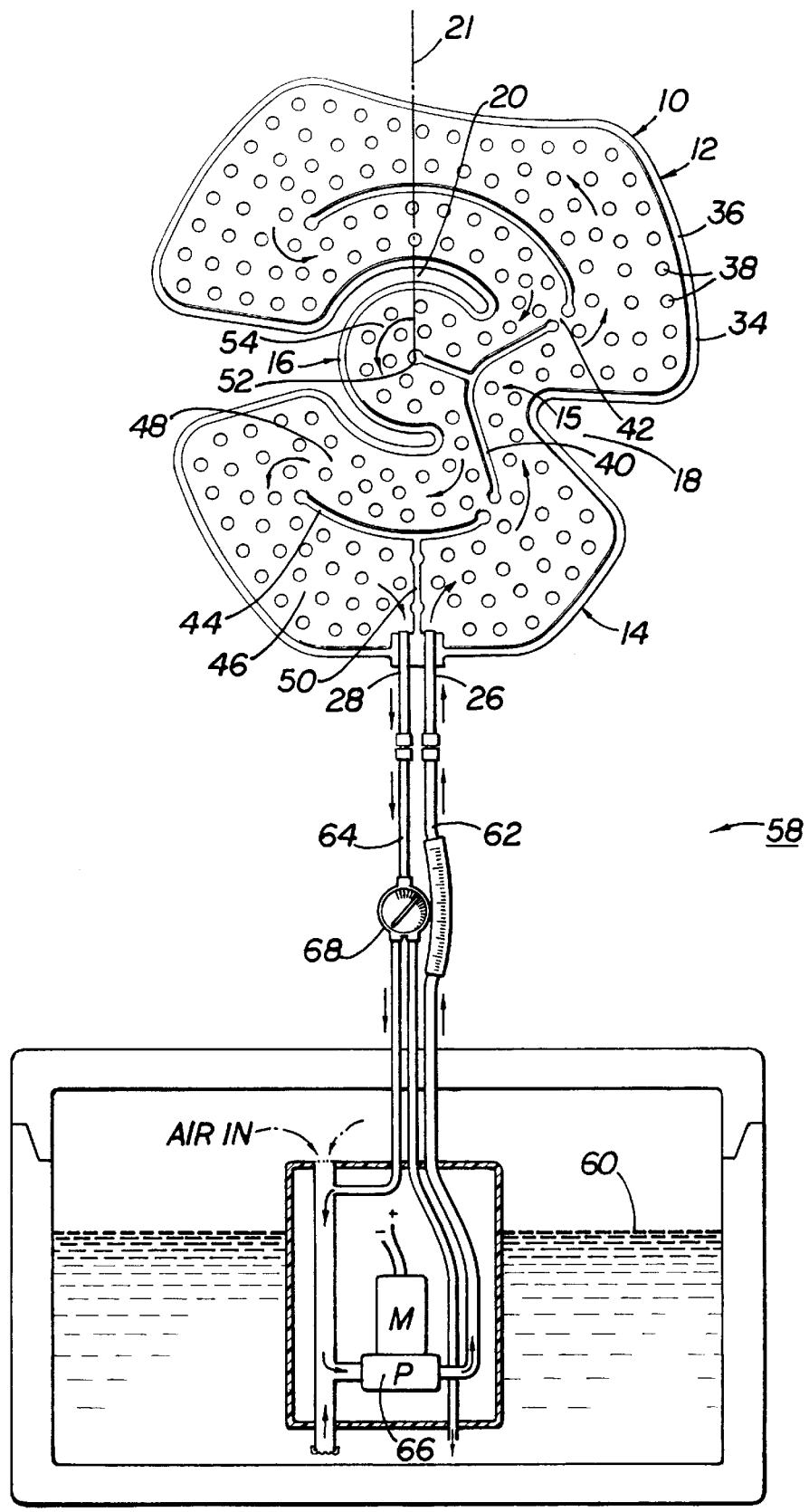
FIG. 3 shows a quasi-schematic view of a cold therapy system in which flexible therapeutic pads according to the present invention may be employed.

FIG. 3 shows pad 10 employed within a thermal therapy system 58. System 58 generally includes a reservoir 60 communicating with pad 10 via an inlet tube 62 and exhaust tube 64 which connect in turn to the inlet port 26 and exhaust port 28 of pad 10. Pad 10 may be configured to allow, as desired, inlet tube 62 and exhaust tube 64 to be connected to either of the ports interchangeably, depending upon whether the user desires to have the thermal medium or fluid 9 first flow in the peripheral flow path 46 or interior flow path 54, if that matters to the user. Reservoir 60 may be a conventional ice chest which contains ice and water, for example, and may contain a pump which feeds inlet tube 62 with pressured fluid or applies a vacuum on exhaust tube 64. Pump 66 is preferably, but need not be, operated with battery or low DC voltage for safety purposes (among other reasons). Pump 66 may provide a constant flow rate, constant pressure or be structured and employed as otherwise desired. It may, if desired, be modulated with feedback from temperature, velocity or pressure sensors within the pad 10, tubes 62 and 64, or as otherwise desired to regulate flow rate, flow velocity, temperature and heat exchange properties of pad 10. For a simple example, temperature within the reservoir 60 and the drop across pad 10 may be monitored in order to modulate or control operation of the pump and recirculation of fluid within tubes 62 and 64 to regulate temperature of thermal medium or fluid 9 within the pad 10.

Valve 68 may be of any desired configuration to vary the flow rate to inlet tube 62, exhaust tube 64, or both, or to vary the bypass or recirculation flow in constant pad fluid flow units. A thermometer in or on any of the tubing or otherwise located may be employed in a manually regulated system according to which the user manually adjusts the valve to affect flow and residence time of fluid in pad 10, recirculation of fluid to pad 10, or as otherwise desired in order to regulate the temperature of the fluid 9 in pad 10.

Figure 4:
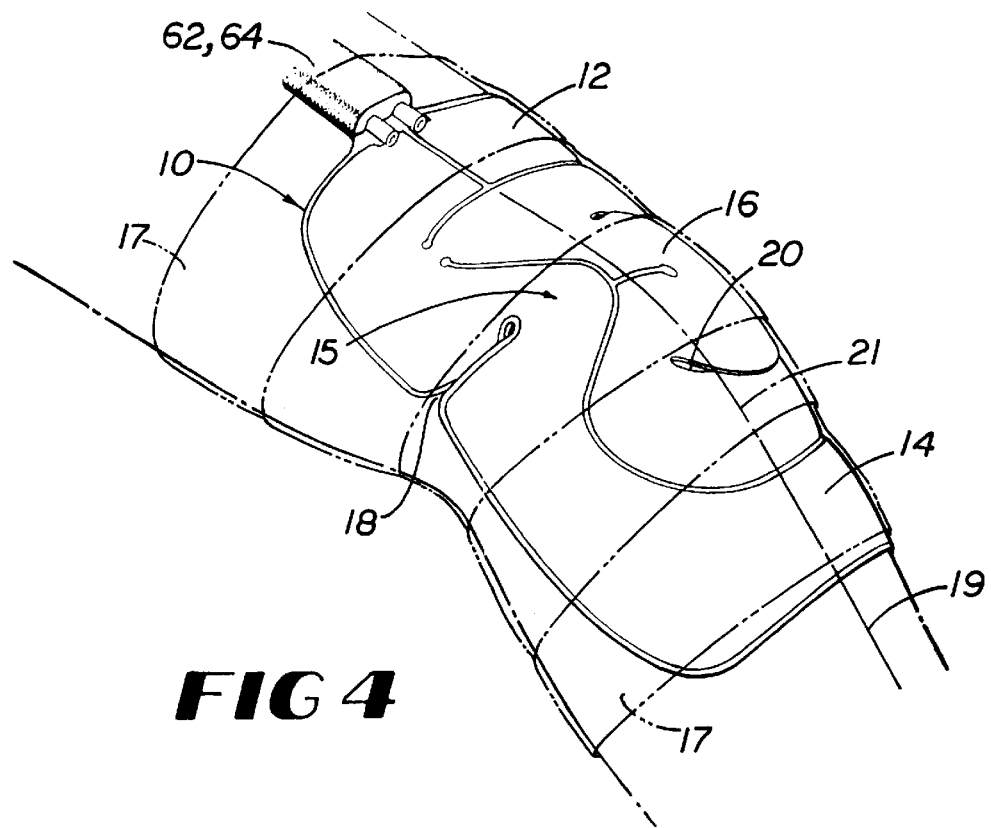
FIG. 4 shows the pad of FIGS. 1A to 1C applied to patient's knee joint.
Figure 4A:
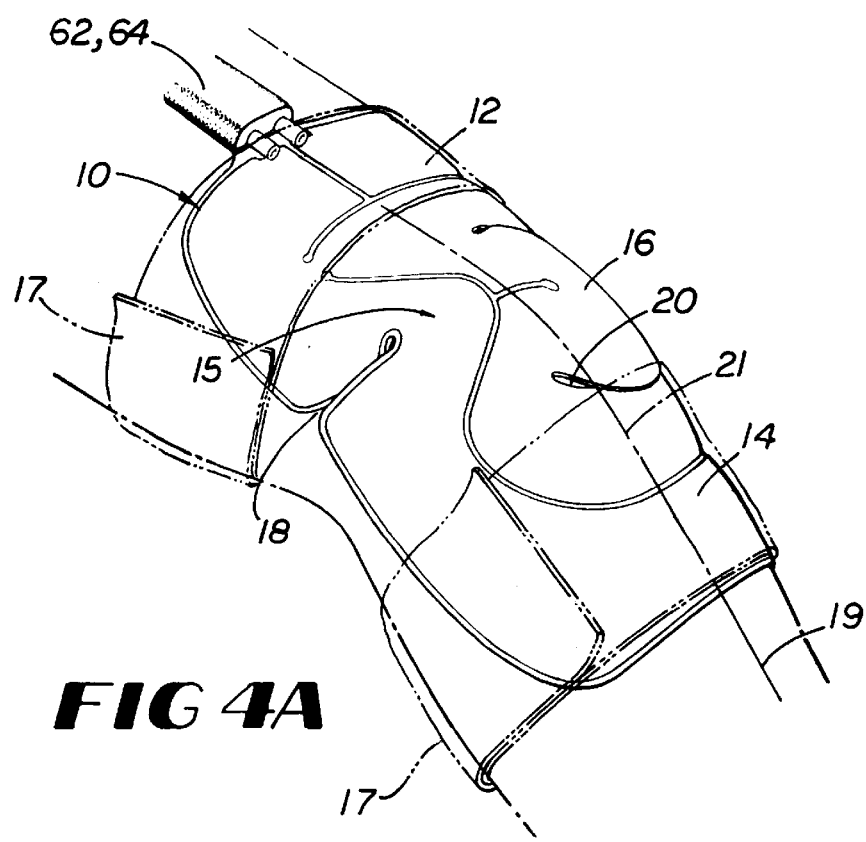
FIG. 4A shows an embodiment of a flexible therapeutic pad according to the present invention with a partial backing of hook and loop fastener material for retention on the patient's joint.
Figure 4B:
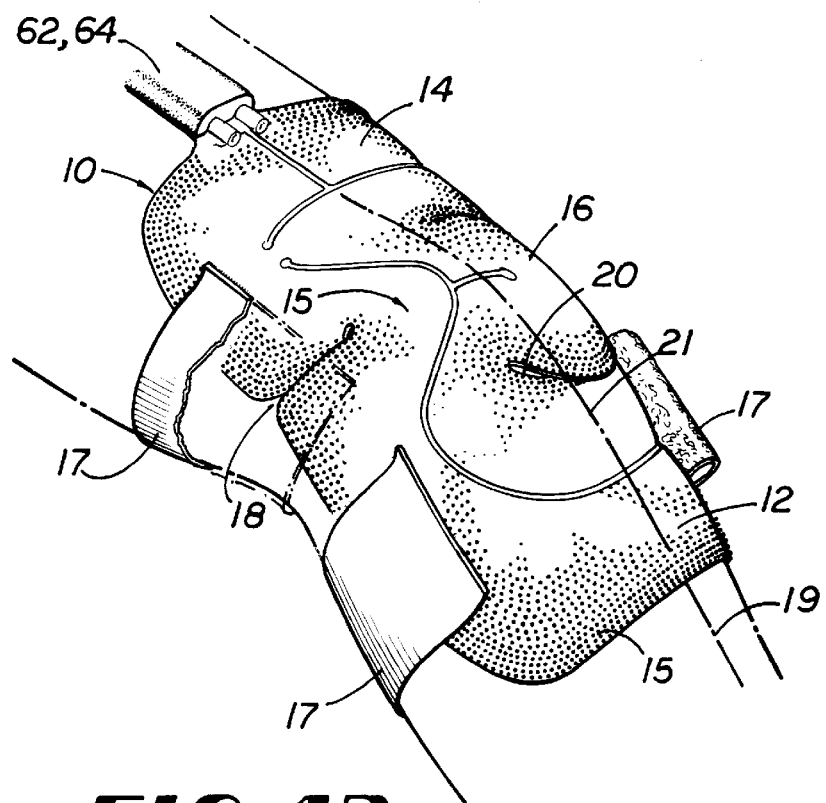
FIG. 4B shows an embodiment of a flexible therapeutic pad according to the present invention which employs hook and loop fastener straps for retention to the patient.
Figure 5:
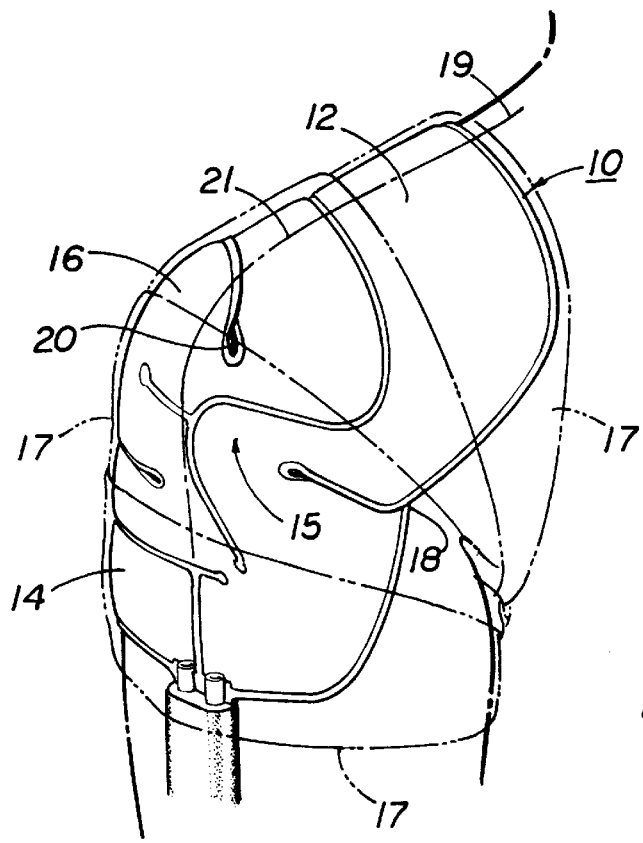
FIG. 5 shows the pad of FIGS. 1A to 1C applied to a patient's shoulder.

FIGS. 4 and 5 show pad 10 on the knee and shoulder respectively. They show inlet 26 and exhaust 28 ports oriented (in one way) on the limb in which the knee or shoulder joint is found, respectively. They show the peripheral discontinuities 20 of the pad relative to the proximal/distal axis 19 of the wearer's limb, which allows pads 10 of the present invention to flex, remain comfortable and convenient and nevertheless provide appropriate heat transfer. FIG. 4A shows a hook or loop pad backing on pad 10 which may be employed in combination with a strap featuring the complimentary hook and loop structure in order to secure pad 10 to the patient's body. FIG. 4B shows hook and loop straps more conventionally employed to secure the pad 10 to the body. Other conventional or unconventional wraps, straps or other structures may be employed to position and secure the pad 10 to the user.

In use, the patient applies first member 12, second member 14 and, if appropriate, center member 16 to the applicable body part adjacent a knee or shoulder joint, in a manner in which ports 26 and 28 are oriented generally on the limb in which the joint is found. Such application can occur before or after connecting the pad 10 to the system 58. Hook and loop fasteners or other wrapping or straps as shown in FIGS. 4, 4A, 4B and 5 may be employed in a conventional manner. Temperature in a manually regulated system may be regulated by controlling valve 68 and amount of ice, water and/or heat medium in reservoir 60.

The present invention considers pad 10 in a broader sense as a heat exchanger than other, previous multijoint pad designs appear to do. It recognizes that optimum heat transfer is achieved by providing components optimally shaped and dimensioned for wrapping around opposite limbs or body parts surrounding a joint, but it recognizes the real world advantages of a multijoint pad which offers clear advantages in the market against a product line that requires three or more corresponding separate pads to cover the same applications. It recognizes that there is no need for unwavering adherence to notions of symmetry, although symmetry may be appropriate where a pad can be configured if structured according to the present invention to conform to body members surrounding the joint in order to allow them to flex and still retain contact with the pad 10 without the pad 10 becoming occluded.

The present invention also recognizes the value of regulating flow velocity within the pad, affecting local flow velocity in order for localized control of heat transfer imparted by the pad, controlling thermal conductivity, thickness and other parameters of the pad components themselves and other physical factors in order to induce or impart accentuated heat transfer on a localized basis where it is needed the most. Other shapes and structures can carry out the broader philosophy of the present invention, in addition to pads simply made according to the three plan aspect illustrations shown above. Those structures obviously fall within the scope and spirit of the present invention and should be considered a part of it.

What is claimed is:

1. A therapy pad for imparting thermal therapy to a patient's joint, comprising:
   a. a first layer and a second layer of flexible material connected at predetermined locations and dimensioned in plan aspect to form:
      (i) a first member; and
      (ii) a second member in fluid communication with the first member;
      (iii) a conduit connecting the first member and the second member;
   b. an inlet port communicating with one of the first or second members;
   c. an exhaust port communicating with one of the first or second members;
   d. the pad adapted to be positioned such that, when worn by the patient:
      (i) the inlet and exhaust ports are oriented generally on a limb in which the joint is found;
      (ii) the first member conforms itself at least partially about the limb on a first side of the joint;
      (iii) the second member conforms itself to the limb on a second side of the joint, whereby the second side is opposite the joint from the first side;
      (iv) the conduit is not substantially centered on the joint when the pad is applied for imparting thermal therapy to the patient when applied for imparting thermal therapy;
      (v) the joint thereby being permitted to flex without substantially disturbing the conformity of the pad members to the limb, and with minimal occlusion in the pad;
   wherein the pad further comprises a cleft between the first and second members for imparting additional flexibility to the pad.

2. A pad according to claim 1 in which the first and second members are substantially curved in plan aspect.

3. A pad according to claim 1 in which the first and second members are elongated and the ports are not coaxial.

4. A pad according to claim 1 further comprising a foam layer attached to one of the first layers and said second layers.

5. A pad according to claim 1 further comprising a center member located substantially between the first and second members.

6. A pad according to claim 5 in which the center member extends from one of the first and second members.

7. A pad according to claim 1 further comprising at least one flowpath boundary connecting the first layer and second layer in order to form at least one fluid flowpath in at least one of the first and second members.

8. A pad according to claim 7 in which the flowpath boundary extends substantially continuously through portions of the first and second members to define at least part of a fluid flowpath circuit connecting the inlet port and the exhaust port.

9. A pad according to claim 1 in which the first layer features thermal transfer properties different from the second layer.

10. A pad according to claim 1 which is shaped substantially in plan aspect to resemble the Greek capital letter Sigma.

11. A pad according to claim 1 which is shaped substantially in plan aspect to resemble the letter C.

12. A pad according to claim 1 which is shaped substantially in plan aspect to resemble the letter O.

13. A pad according to claim 1 in which the inlet and exhaust ports are aligned substantially on a centerline of the pad.

14. A pad according to claim 1 in which the inlet and exhaust ports are not aligned substantially on a centerline of the pad.

15. A thermal therapy pad, comprising:
   a. a first layer of flexible material dimensioned in plan aspect to correspond in shape substantially to the Greek letter sigma thus including:
      (i) a first member corresponding to the upper stroke of the sigma;
      (ii) a second member corresponding to the lower stroke of the sigma;
      (iii) a center member corresponding in location to the stem point of the sigma; and
      (iv) a cleft between the first and second members aligned substantially with the center member corresponding in location to the interior of the sigma stem angle;
   b. a second layer of flexible material dimensioned in plan aspect to correspond to the shape of the first layer;
   c. at least one edge bond connecting the first and second layers about their edges;
   d. at least one flowpath boundary connecting the first layer and second layers in order to form at least one fluid flowpath in at least one of the first and second members;
   e. an inlet port communicating with the fluid flowpath in one of the first and second members;
   f. an exhaust port communicating with the fluid flowpath in one of the first and second members;
   g. the pad adapted to be positioned for imparting thermal therapy to a joint:
      (i) the inlet and exhaust ports being oriented generally on a limb in which the joint is found so that:
      (ii) one of the first and second members conforms itself at least partially about a portion of the limb on a first side of the joint on which the other of the members is not conformed;
      (iii) the other member conforms itself to the limb on a second side of the joint;
      (iv) the center member is aligned substantially with a joint hinge; and
      (v) the joint is accordingly permitted to flex without substantially disturbing the conformity of the pad members to the limb and thus without substantially compromising between the effectiveness of the thermal transfer imparted by the pad and the flexibility of the joint.

16. A pad according to claim 15, in which the first and second members correspond to the upper stroke and serif and lower stroke and serif, respectively, of the sigma.

17. A pad according to claim 15, in which the material from which the first layer is made features different heat transfer properties from the material from which the second layer is made.

18. A pad according to claim 15, in which the first layer features heat transfer properties different from the second layer.

19. A thermal therapy pad, comprising:
   a. a first layer of flexible material dimensioned in plan aspect to include:
      (i) a first member;
      (ii) a second member in fluid communication with the first member; and
      (iii) a center member in fluid communication with the first and second members;
   b. a second layer of flexible material dimensioned in plan aspect to correspond to the shape of the first layer;
   c. at least one edge bond connecting the first and second layers adjacent to their edges;
   d. at least one peripheral flowpath boundary extending substantially continuously through portions of the first and second members and connecting the first layer and second layers in order to form a peripheral flowpath and a middle flowpath;
   e. at least one interior flowpath boundary extending through portions of the center member and connecting the first and second layers to form an interior flowpath;
   d. an inlet port communicating with the peripheral flowpath in one of the first and second members;
   f. an exhaust port communicating with the peripheral flowpath in one of the first and second members;
   g. a differential boundary extending substantially between the peripheral flowpath boundary and the inlet and exhaust ports;
   h. the pad adapted to be positioned for imparting thermal therapy to a joint:
      (i) to orient the inlet and exhaust ports generally on a limb in which the joint is found so that:
      (ii) one of the first and second members conforms itself at least partially about a portion of the limb on a first side of the joint on which the other member is not conformed;
      (iii) the other member conforms itself to the limb on a second side of the joint;
      (iv) the center member is aligned substantially with a joint hinge; and
      (v) the joint is thereby permitted to flex without substantially disturbing the conformity of the pad members to the limb and thus without substantially compromising between the effectiveness of the thermal transfer imparted by the pad and the flexibility of the joint.

20. A pad according to claim 19, in which the interior flowpath communicates with the middle flowpath and the middle flowpath communicates with the peripheral flowpath.

21. A pad according to claim 19, in which the middle flowpath and interior flowpath feature smaller average cross-sections than the peripheral flowpath in order to increase fluid velocity in the middle and interior flowpath and thereby increase thermal transfer rate in their vicinity.

22. A pad according to claim 19, in which the peripheral flowpath boundary is connected to the interior flowpath boundary and the differential flowpath boundary.

23. A pad according to claim 19, in which the peripheral flowpath boundary contains at least one gap.

24. A pad according to claim 19, in which the first layer features thermal transfer properties different from the second layer.

25. A thermal therapy pad, comprising:
   a. a first layer of flexible material dimensioned in plan aspect to correspond in shape substantially to the Greek letter sigma thus including:
      (i) a first member corresponding to the upper stroke of the sigma;
      (ii) a second member corresponding to the lower stroke of the sigma; and (iii) a center member corresponding in location to the stem point of the sigma; and
(iv) a cleft between the first and second members aligned substantially with the center member corresponding in location to the interior of the sigma stem angle;
b. a second layer of flexible material dimensioned in plan aspect to correspond to the shape of the first layer;
c. at least one edge boundary connecting the first and second layers about their edges;
d. at least one peripheral flowpath boundary extending substantially continuously through portions of the first and second members and connecting the first layer and second layers in order to form an peripheral flowpath and a middle flowpath;
e. an inlet port communicating with the peripheral flowpath in one of the first and second members;
f. an exhaust port communicating with the peripheral flowpath in one of the first and second members; and
g. a differential boundary extending substantially between the peripheral flowpath boundary and the inlet and exhaust ports;
h. the pad adapted to be positioned for imparting thermal therapy to a joint:
(i) the inlet and exhaust ports oriented generally on a limb in which the joint is found so that:
(ii) one of the first and second members conforms itself at least partially about a portion of the limb on a first side of the joint on which the other member is not conformed;
(iii) the other member conforms itself to the limb on a second side of the joint;
(iv) the center member is aligned substantially with a joint hinge; and
(v) the cleft is placed in the vicinity of the hinge to allow the joint to flex without substantially disturbing the conformity of the pad members to the limb and thus without substantially compromising between the effectiveness of the thermal transfer imparted by the pad and the flexibility of the joint.

26. A pad according to claim 25, in which the interior flowpath communicates with the middle flowpath and the middle flowpath communicates with the peripheral flowpath.

27. A pad according to claim 25, in which the middle flowpath and interior flowpath feature smaller average cross-sections than the peripheral flowpath in order to increase fluid velocity in the middle and interior flowpath and thereby increase thermal transfer rate in their vicinity.

28. A pad according to claim 25, in which the peripheral flowpath boundary is connected to the interior flowpath boundary and the differential flowpath boundary.

29. A pad according to claim 25, in which the peripheral flowpath boundary contains at least one gap.

30. A pad according to claim 25, in which the first layer features thermal transfer properties different from the second layer.

31. A pad according to claim 25, in which the cleft is substantially symmetrical and with an axis of symmetry oriented substantially parallel to the first and second members in the direction of the sigma strokes.

32. A pad according to claim 25, in which the cleft is positioned to be aligned substantially along an axis of the joint hinge.

33. A system for imparting cold therapy to a variety of joints in a patient's body, comprising:
a. a chilled fluid reservoir in the form of an ice chest;
b. tubing communicating with the fluid reservoir and adapted to communicate with a thermal therapy pad;
c. a pump communicating with the conduit adapted to circulate the fluid in the reservoir and the pad;
d. a valve adapted to regulate temperature of the fluid in the conduit; and
e. a thermal therapy pad communicating with the tubing and adapted to induce hypotherapy effectively in the patient's joint, which thermal therapy pad comprises:
(i) a first chamber adapted in shape to fit a portion of the patient's limb on a first side of the patient's joint;
(ii) a second chamber adapted in shape to fit a portion of the patient's limb on a second side of the joint;
(iii) a center chamber adapted in shape to overlie a portion of the joint;
(iv) the chambers in fluid communication with each other and with the conduit;
(v) the pad, when worn by the patient, being asymmetrical in shape about an axis formed by a line extending from the tubing adjacent to the pad, the first chamber, the joint, and second chamber thereby substantially unrestrained as they track motion of their respective portion of the patient's limb in the vicinity of the joint.

34. A pad according to claim 33, further comprising a third chamber in fluid communication with the first and second chambers.

35. A pad according to claim 34, in which the first, second and third chambers correspond in location to the strokes of the letter E.

36. A pad according to claim 34, in which the first, second and third chambers are in fluid communication with each other at one end of each chamber.

37. A pad according to claim 33, in which the first and second chambers include at least one flow boundary which creates at least two fluid flow paths in each chamber.

38. A pad according to claim 37, in which one fluid flowpath is smaller in cross section than another fluid flowpath.

* * * * *